(12) United States Patent
Bao et al.

(10) Patent No.: US 6,842,261 B2
(45) Date of Patent: Jan. 11, 2005

(54) INTEGRATED CIRCUIT PROFILE VALUE DETERMINATION

(75) Inventors: Junwei Bao, Santa Clara, CA (US); Wen Jin, Sunnyvale, CA (US); Emmanuel Drege, San Jose, CA (US); Srinivas Doddi, Fremont, CA (US); Vi Vuong, Fremont, CA (US)

(73) Assignee: Timbre Technologies, Inc., Santa Clara, CA (US)

(*) Notice: Subject to any disclaimer, the term of this patent is extended or adjusted under 35 U.S.C. 154(b) by 325 days.

(21) Appl. No.: 10/228,692

(22) Filed: Aug. 26, 2002

(65) Prior Publication Data

US 2004/0039473 A1 Feb. 26, 2004

(51) Int. Cl.$^7$ .................. G01B 11/02; G01N 21/88; G06F 19/00; H01L 21/00
(52) U.S. Cl. .................. 356/636; 356/237.5; 438/7; 438/16; 702/189; 700/121
(58) Field of Search .................. 356/237.5, 629–640; 250/559.22, 559.24; 438/7, 16, 14; 702/189, 356, 155, 70, 71, 127, 159; 700/121

(56) References Cited

U.S. PATENT DOCUMENTS

| | | | | |
|---|---|---|---|---|
| 6,609,086 B1 | * | 8/2003 | Bao et al. | 702/189 |
| 6,660,542 B1 | * | 12/2003 | Stirton | 438/16 |
| 6,721,691 B2 | * | 4/2004 | Bao et al. | 702/189 |
| 6,775,015 B2 | * | 8/2004 | Bischoff et al. | 356/636 |
| 6,785,009 B1 | * | 8/2004 | Stirton et al. | 356/625 |
| 2002/0113966 A1 | * | 8/2002 | Shchegrov et al. | 356/369 |
| 2003/0187604 A1 | * | 10/2003 | Drege et al. | 702/119 |
| 2004/0017574 A1 | * | 1/2004 | Vuong et al. | 356/625 |
| 2004/0090629 A1 | * | 5/2004 | Drege et al. | 356/445 |

* cited by examiner

*Primary Examiner*—Layla G. Lauchman
(74) *Attorney, Agent, or Firm*—Morrison & Foerster LLP

(57) ABSTRACT

A profile parameter value is determined in integrated circuit metrology by: a) determining a diffraction signal difference based on a measured diffraction signal and a previously generated diffraction signal; b) determining a first profile parameter value based on the previously generated diffraction signal; c) determining a first profile parameter value change based on the diffraction signal difference; d) determining a second profile parameter value based on the first profile parameter value change; e) determining a second profile parameter value change between the first and second profile parameter values; f) determining if the second profile parameter value change meets one or more preset criteria; and g) when the second profile parameter value change fails to meet the one or more preset criteria, iterating c) to g) using as the diffraction signal difference in the iteration of step c), a diffraction signal difference determined based on the measured diffraction signal and a diffraction signal for the second profile parameter value previously determined in step d), and as the first profile parameter value in the iteration of step e), the second profile parameter value previously determined in step d).

45 Claims, 8 Drawing Sheets

INTEGRATED CIRCUIT PROFILE VALUE DETERMINATION

BACKGROUND

1. Field of the Invention

The present application relates to integrated circuit (IC) metrology, and more particularly to a sample structure profile determining method in an optical metrology system.

2. Related Art

The use of integrated circuit (IC) metrology has been successful for measuring sample structures. With the progress of deep sub-micron technology, the accuracy and efficiency of sample structure profile measurement are becoming increasingly critical. Examples of a sample structure comprise IC and test structure on a wafer.

For example, an optical metrology system employs a light source to beam light on a wafer structure. The diffracted light is then measured as a diffraction signal. In turn, regression-based methods or library-based methods can be used for determining the sample structure profile that matches the measured diffraction signal.

In one approach, in order to find a match, the measured diffraction signal is compared with previously generated (pre-generated) diffraction signals in a diffraction signal library. These pre-generated diffraction signals are typically simulated by using a rigorous coupled-wave analysis (RCWA) method.

An associated profile parameter, which characterizes a sample structure profile that corresponds to the nearest diffraction signal, is typically determined using pre-generated profile parameters found in a profile library. Furthermore, a profile parameter value change is calculated according to the diffraction signal change. This calculated profile parameter value change is evaluated to determine whether the profile parameter value change satisfies preset criteria. If the preset criteria are met, the new profile parameter value, which is calculated by adding the profile parameter value change to the associated profile parameter, is considered an acceptable approximation of the true profile parameter value corresponding to the measured diffraction signal. Otherwise, another diffraction signal is simulated based on this newly calculated profile parameter value by using RCWA method (or some other rigorous or approximation methods) in order to get a new diffraction signal change between the measured diffraction signal and the newly simulated diffraction signal. Several iterations of the profile parameter value computation and the diffraction signal simulation might be needed to finally converge to a profile parameter value that is considered an acceptable approximation of the true profile parameter value.

The conventional computing method for calculating a profile parameter value change from a diffraction signal change is to use the inverse of a Jacobian matrix from a conversion matrix library or directly calculated during the optimization process. (The definition of the inverse of a Jacobian matrix is provided in the detailed description.) The Jacobian matrix reflects sensitivities of sample structure profile parameters, meaning the magnitude of change of a diffraction signal corresponding to a change in a profile parameter value. However, when these sensitivities as reflected by the Jacobian matrix are highly correlated, this conventional approach may lack convergent speed and/or accuracy.

To increase the convergent speed, large number of CPUs or supercomputers are used. However, adding multiple CPUs or supercomputers not only increases the production cost, but also may not solve the profile parameter value convergence/inaccuracy problem. Moreover, beside the method described above, other optimization methods also do not solve the profile parameter value convergence/inaccuracy problem.

Through experiments, optical metrology engineers determine if the profile parameters in a profile library are generated from certain ways of parameterization of the profile, some of the corresponding conversion Jacobian matrices in the conversion matrix library contain highly correlated sensitivities of the sample structure profile parameters. On the other hand, if some other profile parameterization methods are used to generate the profiles in a profile library, the Jacobian matrix high correlation problem, which results in a greater number of iterations to be performed and thus increases processing time, might be avoided. Since no one knows exactly which sample structure profile parameterization will generate an accurate mapping and fast converging profile parameter in a profile library, each optical metrology engineer uses his or her own sample structure profile parameters relying on his or her past experience and know-how. As such, multiple profile libraries are typically created for the same sample structure structure. However, in so doing, having to perform optical metrology from different libraries causes inconsistency and confusion in the metrology industry.

SUMMARY

In an exemplary embodiment, a profile parameter value is determined in integrated circuit metrology by: a) determining a diffraction signal difference based on a measured diffraction signal and a previously generated diffraction signal; b) determining a first profile parameter value based on the previously generated diffraction signal; c) determining a first profile parameter value change based on the diffraction signal difference; d) determining a second profile parameter value based on the first profile parameter value change; e) determining a second profile parameter value change between the first and second profile parameter values; f) determining if the second profile parameter value change meets one or more preset criteria; and g) when the second profile parameter value change fails to meet the one or more preset criteria, iterating c) to g) using as the diffraction signal difference in the iteration of step c), a diffraction signal difference determined based on the measured diffraction signal and a diffraction signal for the second profile parameter value previously determined in step d), and as the first profile parameter value in the iteration of step e), the second profile parameter value previously determined in step d).

DESCRIPTION OF DRAWING FIGURES

The present application can be better understood by reference to the following description taken in conjunction with the accompanying drawing figures, in which like parts may be referred to by like numerals:

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

In the following description, an optical metrology system is described to provide an example of a metrology system that can be used with the exemplary embodiments to be described. It is understood that various metrology systems can be used. In a similar manner, although a profile library, a diffraction signal library, and a conversion matrix library are described, a data space comprising profile parameters or a data space comprising diffraction signal parameters from diffraction signals or a data space comprising conversion Jacobian matrices or a data space comprising corresponding metrology signals can also be used.

Figure 1:
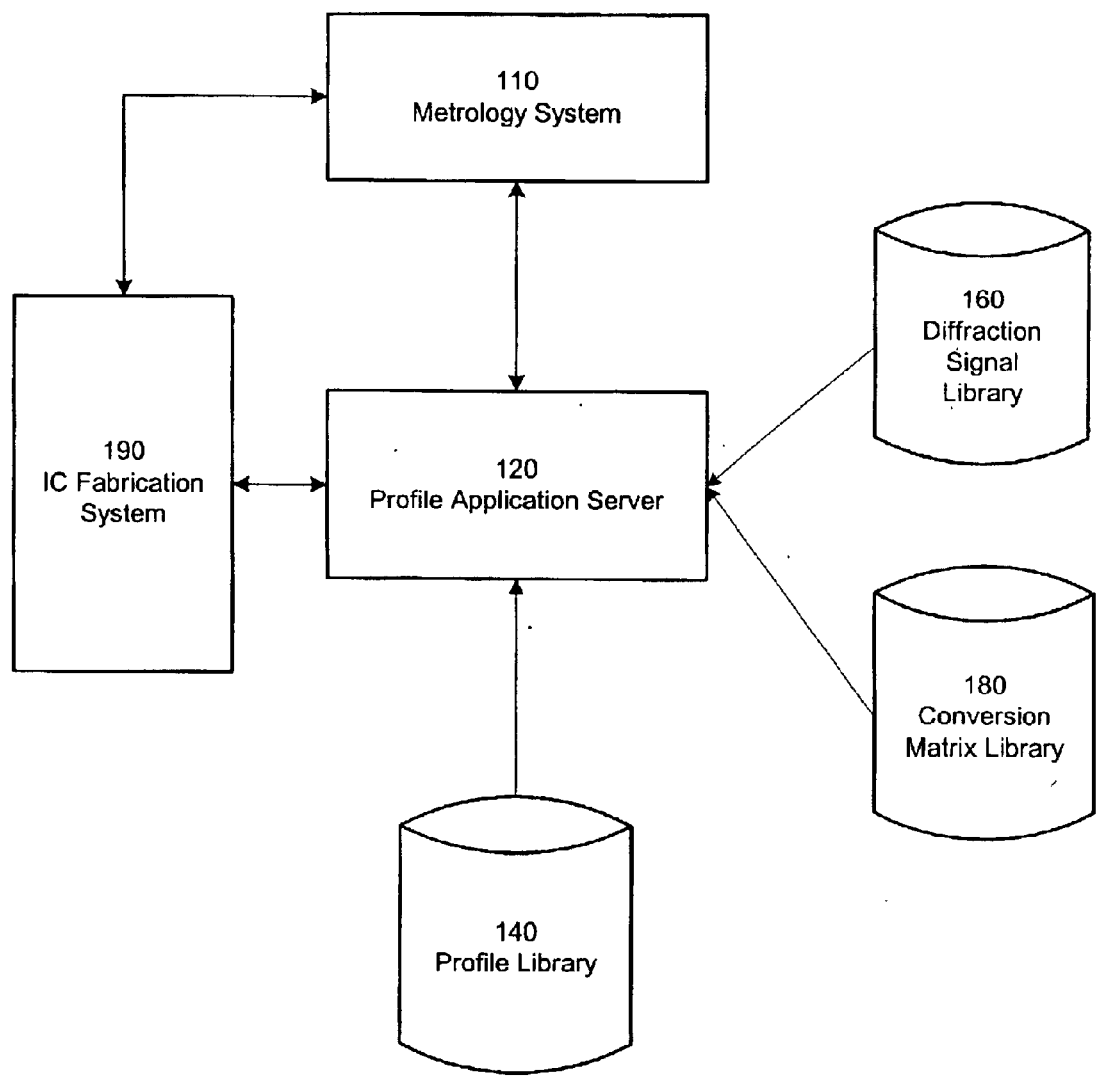
FIG. 1 is an architectural diagram illustrating the use of optical metrology to measure the diffraction signals off wafer structures in a library-based metrology system in accordance with one embodiment.

Referring now to FIG. 1, an architectural diagram of a library-based optical metrology system is shown in accordance with one embodiment. Diagram 100 comprises a metrology system 110, a profile application server 120, a profile library 140, a diffraction signal library 160, a conversion matrix library 180, and an IC fabrication system 190.

Metrology system 110 may be an optical metrology system, electron metrology system, and the like. Examples of optical metrology systems include spectroscopic ellipsometers and reflectometers. Examples of electron metrology systems include critical dimension-scanning electron microscopes (CD-SEMs). The common characteristic of these systems is that one can simulate the response of a detected signal from a sample structure, but cannot determine the structure directly from the detected signal.

Profile application server 120 may be a device, software, or firmware capable of executing profile determining methods and procedures.

Profile library 140 may be a physical library in a storage device or a data store in a computer memory or a data store in a storage device. Profile library 140 includes a collection of previously generated (pre-generated) profile parameters created from the sample structure profile parameters of sample structure profiles.

Diffraction signal library 160 may be a physical library in a storage device or a data store in a computer memory or a data store in a storage device. Simulated by RCWA or other methods, diffraction signal library 160 comprises a collection of diffraction signals under ideal hardware specification and ideal material properties of the testing sample structures to be profiled, where the ideal hardware specification and ideal material properties may have been provided as nominal values by a manufacturer. Each pre-generated diffraction signal and its neighborhood in diffraction signal library 160 are associated with one profile parameter and its neighborhood in profile library 140.

Conversion matrix library 180 may be a physical library in a storage device or a data store in a computer memory or a data store in a storage device. Conversion matrix library 180 comprises a collection of pre-calculated Jacobian matrices. The matrices can also be calculated during the profile inversion process. One Jacobian matrix corresponds to one pair of a diffraction signal and its neighborhood in diffraction signal library 160 and the associated profile parameter and its neighborhood in profile library 140.

IC fabrication system 190 may be a lithographic, etching, stripping unit, and the like.

When metrology system 110 is an optical metrology system, metrology system 110 beams light on a wafer structure, measures the diffraction signal, and transmits the measured diffraction signal to the coupled profile application server 120.

Profile application server 120 accesses diffraction signal library 160 to find a matching or nearest previously generated (pre-generated) diffraction signal by comparing the received diffraction signal with the pre-generated diffraction signals. After finding the matching or nearest diffraction signal to the measured diffraction signal, profile application server 120 accesses profile library 140 to find the associated profile parameter. Profile application server 120 also accesses conversion matrix library 180 to find the corresponding conversion Jacobian matrix. Note that the pre-simulated diffraction signal, profile parameters, and conversion Jacobian matrix can be stored and thus obtained from a single library.

Profile application server 120 computes the diffraction signal change between the measured diffraction signal and the nearest pre-generated diffraction signal, and selects a profile determining method to be used to calculate the profile parameter value change according to the degree of correlation among the sensitivities of sample structure profile parameters of the corresponding Jacobian matrix.

In one embodiment, the profile parameter value change can be computed using a profile determination method selected from a set of profile determination methods. For example, in the present embodiment, either a first profile determination method (method A) or a second profile determination method (method B). The profile parameter value change is evaluated in profile application server 120 to determine whether this profile parameter value change meets one or more preset criteria. If the preset criteria are not met, the profile determination method used is iterated. The preset criteria may be that certain error metric value is less than a preset value, or goodness of fit (GOF) is higher than a preset value, or the difference between the profile parameter values of the last two consecutive iterations is less than a preset value. Method A and method B will be described with respect to FIG. 2.

If the profile parameter value change satisfies the preset criteria, the profile parameter value, calculated by adding the profile parameter value change to the associated profile parameter, is considered an acceptable approximation of the true profile parameter value corresponding to the measured diffraction signal. Otherwise, a new diffraction signal is simulated based on the calculated profile parameter value using RCWA method or any other rigorous or simulation method. A new profile parameter value change is computed from the new diffraction signal change between the newly simulated diffraction signal and the measured diffraction signal. The iteration of the profile parameter value computation and the diffraction signal simulation continues until the profile parameter value change meets the preset criteria.

Profile application server 120 makes the profile parameter value, which is considered an acceptable approximation of the true profile parameter value, available to IC fabrication system 190. Alternatively, profile application server 120 transmits the profile parameter value, which is considered an acceptable approximation of the true profile parameter value, back to metrology system 110.

Figure 2:
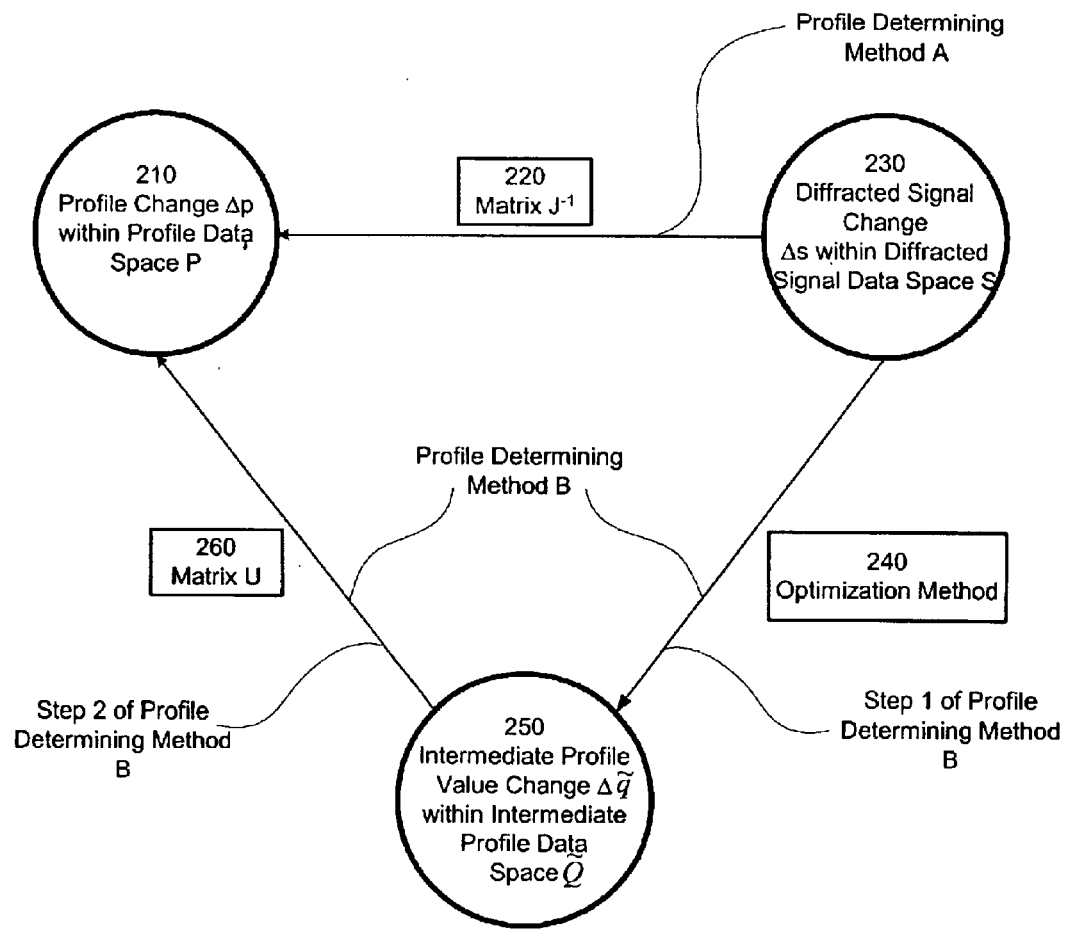
FIG. 2 is a conceptual block diagram illustrating two profile determining methods and the conversion matrices involved in accordance with one embodiment.

Referring now to FIG. 2 in view of FIG. 1, a conceptual block diagram 200 is shown illustrating two profile determining methods used by profile application server 120 to calculate the profile parameter value change Δp 210 from the diffraction signal change Δs 230 in accordance with one embodiment.

After finding a corresponding conversion Jacobian matrix J from conversion matrix library 180, profile application server 120 evaluates this Jacobian matrix J to determine if the matrix J has a degree of correlation above a threshold level. If the degree of correlation is greater than the threshold level, the sensitivities of the sample structure profile parameters of matrix J are highly correlated. In one embodiment, a threshold level of about 0.95 is used. Note, however, that various threshold levels may be used depending on the application.

In one embodiment, when the sensitivities of sample structure profile parameters as provided by Jacobian matrix J are not highly correlated, profile determining method A is used to calculate a profile parameter value change from a diffraction signal data space S to a profile data space P. Profile determining method A directly uses matrix $J^{-1}$ 220, the inverse of Jacobian matrix J, to calculate the profile parameter value change Δp 210 from the diffraction signal change Δs 230. As understood herein, $J^{-1}$ is defined as $J^{-1} \equiv (J^t J)^{-1} J^t$.

When the sensitivities of sample structure profile parameters as provided by Jacobian matrix J are highly correlated, parameter decorrelation is performed. For parameter decorrelation, profile determining method B is used to introduce a third data space, an intermediate profile data space $\tilde{Q}$, to indirectly calculate a profile parameter value change from a diffraction signal data space S to a profile data space P. Specifically, an alternative Jacobian matrix L and a linear transformation matrix U 260 are derived from the Jacobian matrix J. In comparison to the sensitivities of sample structure profile parameters as provided by Jacobian matrix J, the sensitivities of sample structure profile parameter as provided by Jacobian matrix L are not as highly correlated. More specifically, for an entire domain of the profile data space, sensitivities of sample structure profile parameters as provided by L could be correlated. But the degree of correlation for L is expected to be smaller than that of J. Depending on the accuracy required, different Jacobian matrices could be used for different profile points within a profile data space. Or, a single Jacobian matrix could be used for an entire domain of the profile data space.

An intermediate profile parameter value change Δq̃ 250 within the intermediate profile data space $\tilde{Q}$ is computed first from the diffraction signal change Δs 230 by using either local or global optimization method. In turn, the profile parameter value change Δp 210 will be mapped from the intermediate profile parameter value change Δq̃ 250 by using the linear transformation matrix U 260. Examples of local optimization methods are Gauss-Newton method and Levenberg-Marquardt method, and examples of global optimization methods are genetic algorithm and simulated annealing.

As shown in diagram 200 in FIG. 2, profile determining method B comprises two steps. In step 1 of profile determining method B, the intermediate profile parameter value change Δq̃ 250 within a intermediate profile data space $\tilde{Q}$ is computed from the diffraction signal change Δs 230 within a diffraction signal data space S by using an optimization algorithm.

In step 2 of profile determining method B, the profile parameter value change Δp 210 within a profile data space P is mapped from the intermediate profile parameter value change Δq̃ 250 calculated in step 1 by using the linear transformation matrix U 260.

Figure 3:
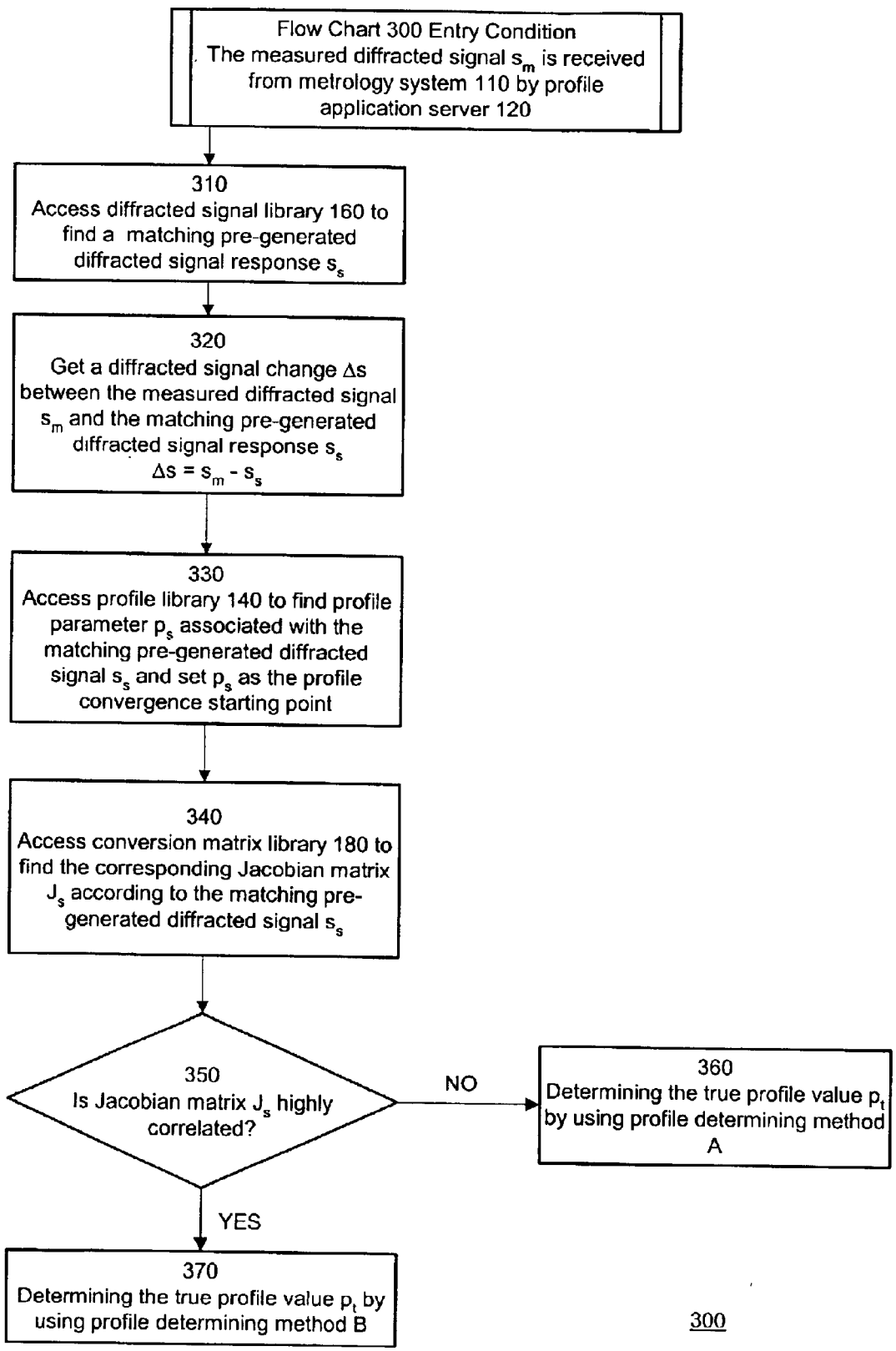
FIG. 3 is a flow chart outlining steps for determining the true profile parameter value by either of the two profile determining methods in accordance with one embodiment.

Referring now to FIG. 3 in view of FIGS. 1 and 2, a flow chart 300 is shown outlining the true profile parameter value $p_t$ convergence steps used by profile application server 120 in accordance with one embodiment.

The entry condition for flow chart 300 is that the measured diffraction signal $s_m$ is already received by profile application server 120 from metrology system 110.

In step 310, profile application server 120 accesses diffraction signal library 160 to find a nearest diffraction signal $s_s$ by comparing the received diffraction signal $s_m$ with the pre-generated diffraction signals. As understood herein, step 310 can also be performed using global optimization techniques.

In step 320, profile application server 120 computes the diffraction signal change Δs between the measured diffraction signal $s_m$ and the nearest diffraction signal $s_s$:

$$\Delta s = s_m - s_s$$

In step 330, profile application server 120 accesses profile library 140 to find the pre-generated profile parameter $p_s$ that characterizes a sample structure profile associated with the diffraction signal $s_s$. This associated profile parameter $p_s$ is the profile convergence starting point for determining $p_t$.

In step 340, profile application server 120 accesses conversion matrix library 180 to find the corresponding conversion Jacobian matrix $J_s$ according to the pre-generated diffraction signal $s_s$. The Jacobian matrix $J_s$ is used to map the neighborhood of $p_s$ to the neighborhood of $s_s$. Specifically, the inverse of $J_s$ is used to obtain the profile parameter value change Δp from the diffraction signal change Δs calculated in step 320.

In step 350, the Jacobian matrix $J_s$ is evaluated by profile application server 120 to determine whether the sensitivities of sample structure profile parameters as provided by $J_s$ are highly correlated. If these sensitivities of sample structure profile parameters are not highly correlated, the profile parameter value considered an acceptable approximation of the true profile parameter value $p_t$ is determined in step 360 by using profile determining method A. Otherwise, if the sensitivities of sample structure profile parameters of $J_s$ are highly correlated, the profile parameter value $p_t$ is determined in step 370 by using profile determining method B.

Figure 4:
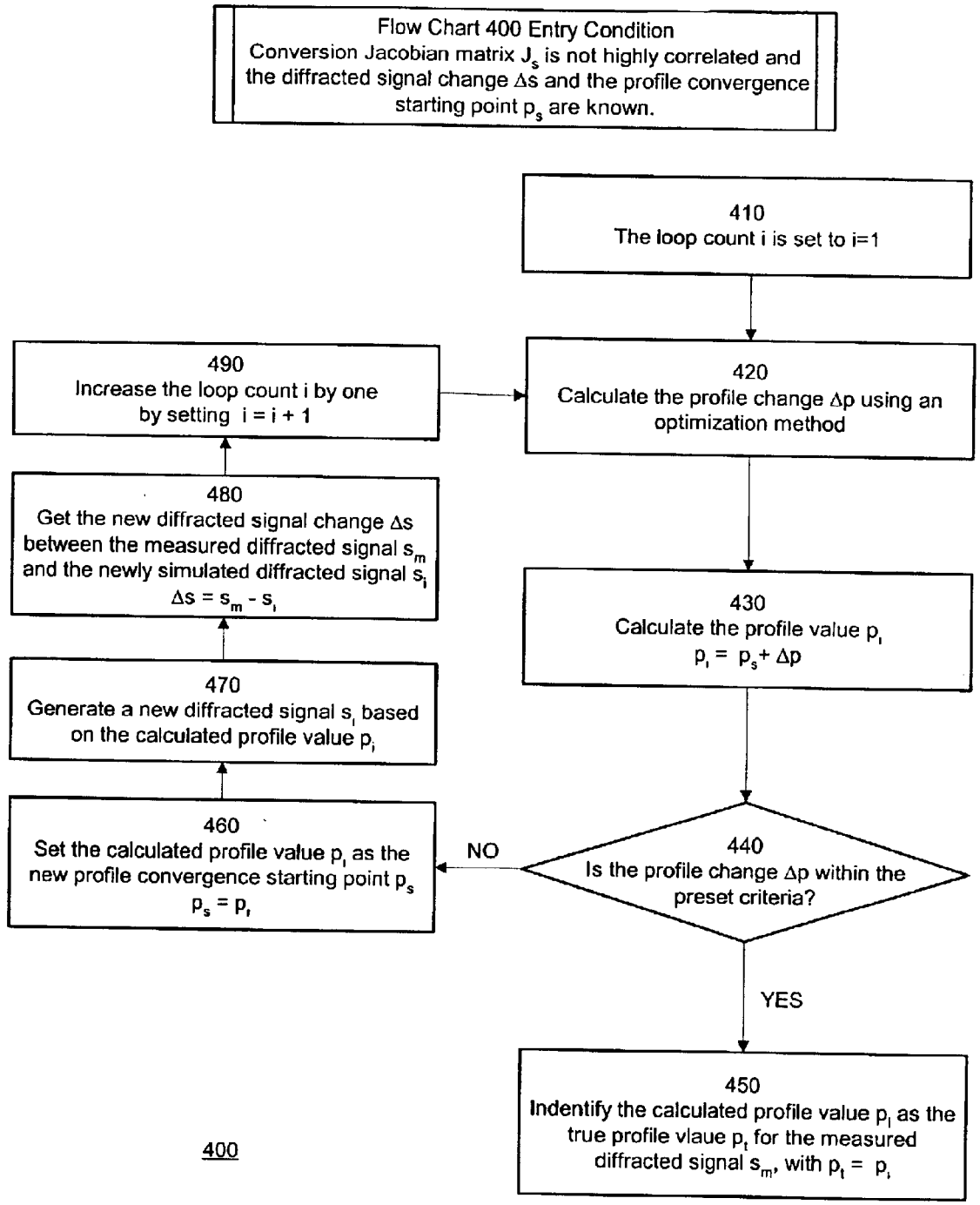
FIG. 4 is a detailed flow chart outlining steps for determining the true profile parameter value by using a first profile determining method in accordance with the embodiment depicted in FIG. 3.

Referring now to FIG. 4 in view of FIG. 3, a detailed flow chart 400 is shown outlining profile determining method A in accordance with one embodiment. Specifically, flow chart 400 is the detailed explanation for step 360 of flow chart 300 in FIG. 3.

The entry condition for flow chart 400 is that the conversion Jacobian matrix $J_s$ is already evaluated (in step 350) as not having highly correlated sensitivities of sample structure profile parameters. The diffraction signal change $\Delta s$ between the measured diffraction signal $s_m$ and the nearest pre-generated diffraction signal $s_s$ is computed (in step 320). The associated profile parameter $p_s$ is obtained from profile library 140 (in step 330). The profile parameter $p_s$, corresponding to the nearest diffraction signal $s_s$, is used as the profile convergence starting point.

In step 410, a loop count i is set to one. The loop count i is used to track the number of profile computing iterations needed to converge to the profile parameter value considered an acceptable approximation of the true profile parameter parameter value $p_t$, which characterizes a sample structure profile corresponds to the measured diffraction signal $s_m$.

In step 420, the profile parameter value change $\Delta p$ is calculated directly through the inverse of Jacobian matrix $J_s$.

Since the change of each profile parameter value p will contribute to the change of the diffraction signal s through the Jacobian matrix $J_s$. The approximation equation between the profile parameter value change $\Delta p$ and the diffraction signal change $\Delta s$ is as follows:

$$\Delta s \approx J_s \Delta p.$$

Therefore, the profile parameter value change $\Delta p$ can be calculated as:

$$\Delta p \approx J_s^{-1} \Delta s.$$

In step 430, the profile parameter value $p_1$ is calculated by adding the profile parameter value change $\Delta p$ to the profile convergence starting point $p_s$:

$$p_1 = p_s + \Delta p$$

where i is the number of iterations for profile parameter value computation and diffraction signal simulation.

In step 440, the profile parameter value change $\Delta p$ calculated in step 420 is evaluated to determine whether this profile parameter value change $\Delta p$ satisfies the preset criteria. The preset criteria may be that certain error metric value is less than a preset value, or goodness of fit (GOF) is higher than a preset value, or the difference between the profile parameter values of the last two consecutive iterations is less than a preset value. One exemplary matching test that is well known in the art is that of minimum mean square error. It is understood that other error metric algorithms may also be used.

In step 450, the profile parameter value change $\Delta p$ meets the preset criteria. Therefore, the profile parameter value $p_1$ calculated in step 430 is deemed as an acceptable approximation of the true profile parameter value $p_t$ for the measured diffraction signal $s_m$.

In step 460, the profile parameter value change $\Delta p$ does not meet the preset criteria. Therefore, the profile parameter value $p_i$ calculated in step 430 is set as the new profile convergence starting point $p_s$:

$$p_s = p_1$$

where i is the number of iterations for the diffraction signal simulation and profile computation.

In step 470, a diffraction signal $s_1$ is simulated by using RCWA method (or another rigorous or approximation method) based on the profile parameter value $p_1$ calculated in step 430.

In step 480, the new diffraction signal change $\Delta s$ between the measured diffraction signal $s_m$ and the newly simulated diffraction signal $s_i$ is calculated as $$\Delta s = s_m - s_1.$$

In step 490, the loop count i is increased by one to keep track the number of diffraction signal simulation and profile computation iterations. The profile parameter value computation loops back to step 420 and the calculation of the simulated diffraction signal and the profile parameter value is iterated until the profile parameter value change $\Delta p$ calculated in step 420 meets the preset criteria. The loop count can be an integer and the iterations can be terminated if the loop count reaches a predetermined maximum value.

The extraction of the profile parameter value considered an acceptable approximation of the true profile parameter parameter value can be viewed as an optimization process. Exemplary optimization techniques include global optimization techniques such as genetic algorithm and local optimization techniques such as the steepest descent algorithm.

Figure 5:
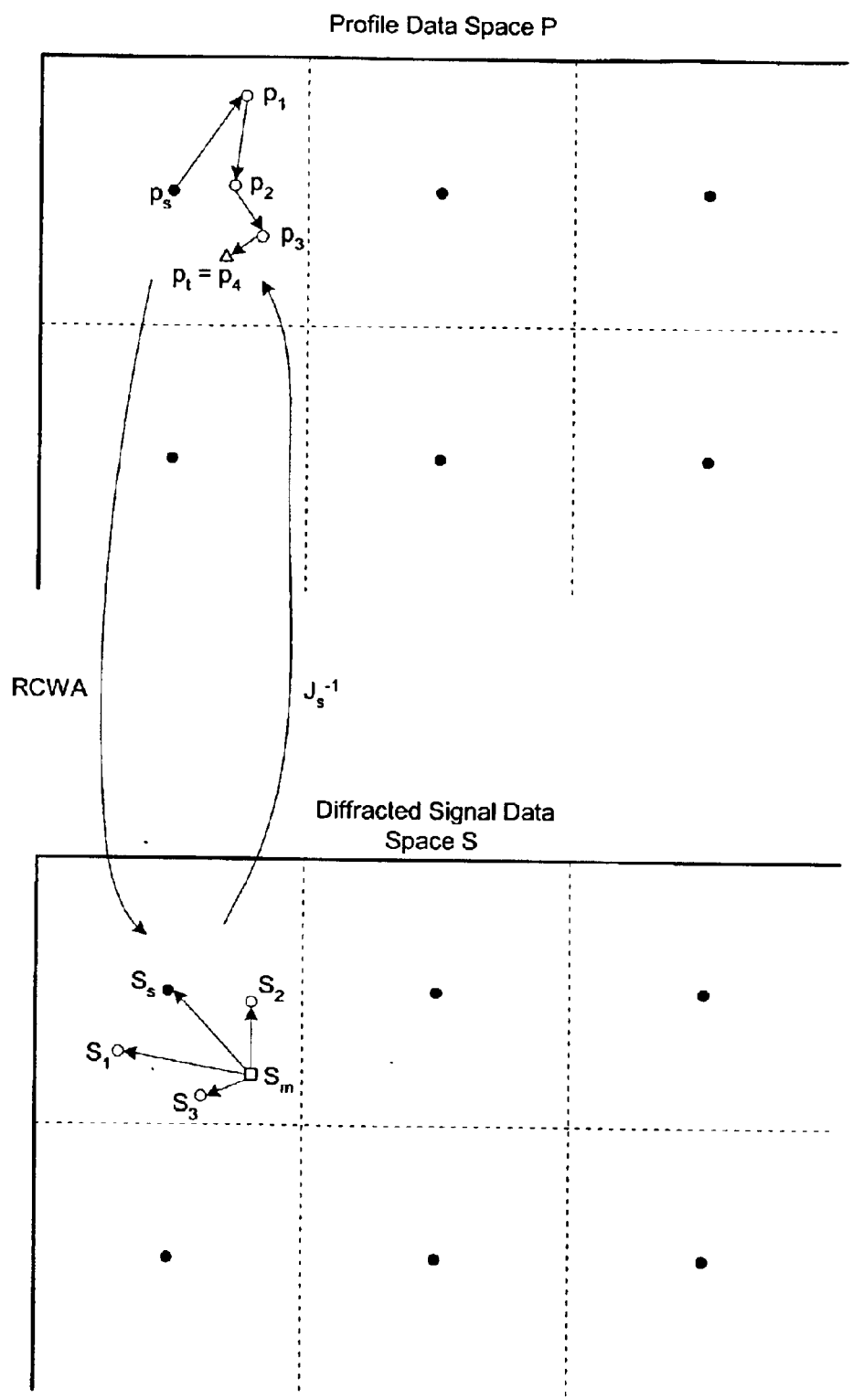
FIG. 5 is an illustration of profile parameter value convergence steps from the initial profile parameter value to the true profile parameter value corresponding to the measured diffraction signal in accordance with one embodiment.

Referring now to FIG. 5 in view of FIGS. 3 and 4, an illustration 500 is shown demonstrating the profile convergence steps in a profile data space P by using profile determining method A. The dashed lines mark the border of the neighborhood of each profile parameter and diffraction signal point. The point of $p_s$ is a pre-generated profile parameter according to the sample structure profile parameters of a wafer structure. The point of $s_s$ is the associated diffraction signal, which is simulated using RCWA method based on the point of $p_s$. The point of $s_m$ is the measured diffraction signal obtained from metrology system 110 by profile application server 120. Since $s_m$ is located in the neighborhood of $s_s$, $s_s$ is the nearest pre-generated diffraction signal for $s_m$ (step 310 of flow chart 300). After calculating the diffraction signal change $\Delta s$ between $s_m$ and $s_s$ (step 320), the associated profile parameter $p_s$ is found for $s_s$ (Step 330) and is set to be the profile convergence starting point. The conversion Jacobian matrix $J_s$ is obtained from conversion matrix library 180 (step 340). The inverse of Jacobian matrix $J_s$ is used to compute the corresponding profile parameter value change from any diffraction signal change within the neighborhood of $s_s$ (step 420 of flow chart 400 in FIG. 4).

Referring still to FIG. 5, four profile parameter values $p_1$, $p_2$, $p_3$, and $p_4$ are calculated by profile determining method A, and three diffraction signals $s_1$, $s_2$, and $s_3$ are simulated by using RCWA methods based on the profile parameter value $p_1$, $p_2$, and $p_3$ respectively. The profile parameter value change $\Delta p$ between $p_3$ and $p_4$ is assumed to meet the preset criteria. Therefore, $p_4$ is determined as the profile parameter value $p_t$ for the measured diffraction signal $s_m$.

Specifically, since $s_m$ is located within the neighborhood of $s_s$, $s_s$ is the nearest diffraction signal for $s_m$. After the associated profile parameter $p_s$ is found for the nearest diffraction signal $s_s$ (step 330 of flow chart 300), the number of iteration loop count is reset to one (step 410 of flow chart 400). The profile parameter value change $\Delta p$ is computed (step 420 of flow chart 400), and $p_1$ is calculated to be the first convergent profile parameter value (step 430 of flow chart 400). The computed profile parameter value change $\Delta p$ is evaluated to determine whether the profile parameter value change $\Delta p$ meets the preset criteria (step 440 of flow chart 400 in FIG. 4). Since the profile parameter value change Δp between $p_1$ and $p_s$ does not meet the preset criteria, the calculated profile parameter value $p_1$ is set to be the new profile convergence starting point (step 460 of flow chart 400). An associated diffraction signal $s_1$ is simulated according to $p_1$ by using RCWA method (step 470 of flow chart 400). According to this new simulated diffraction signal $s_1$, a new diffraction signal change Δs between the measured diffraction signal $s_m$ and the newly simulated diffraction signal $s_1$ is calculated (step 480 of flow chart 400). After the increase of the iteration loop count by one (step 490 of flow chart 400), a new profile parameter value change Δp is calculated and evaluated (step 420 and 440 of flow chart 400). The iteration of profile parameter value computation and diffraction signal simulation continues until the profile parameter value change Δp, which is the profile difference between profile parameter value $p_3$ and $p_4$ meets the preset criteria. Thus, $p_4$ is identified as the approximation of the true profile parameter value $p_t$ for the measured diffraction signal $s_m$ (step 450 of flow chart 400).

Figure 6:
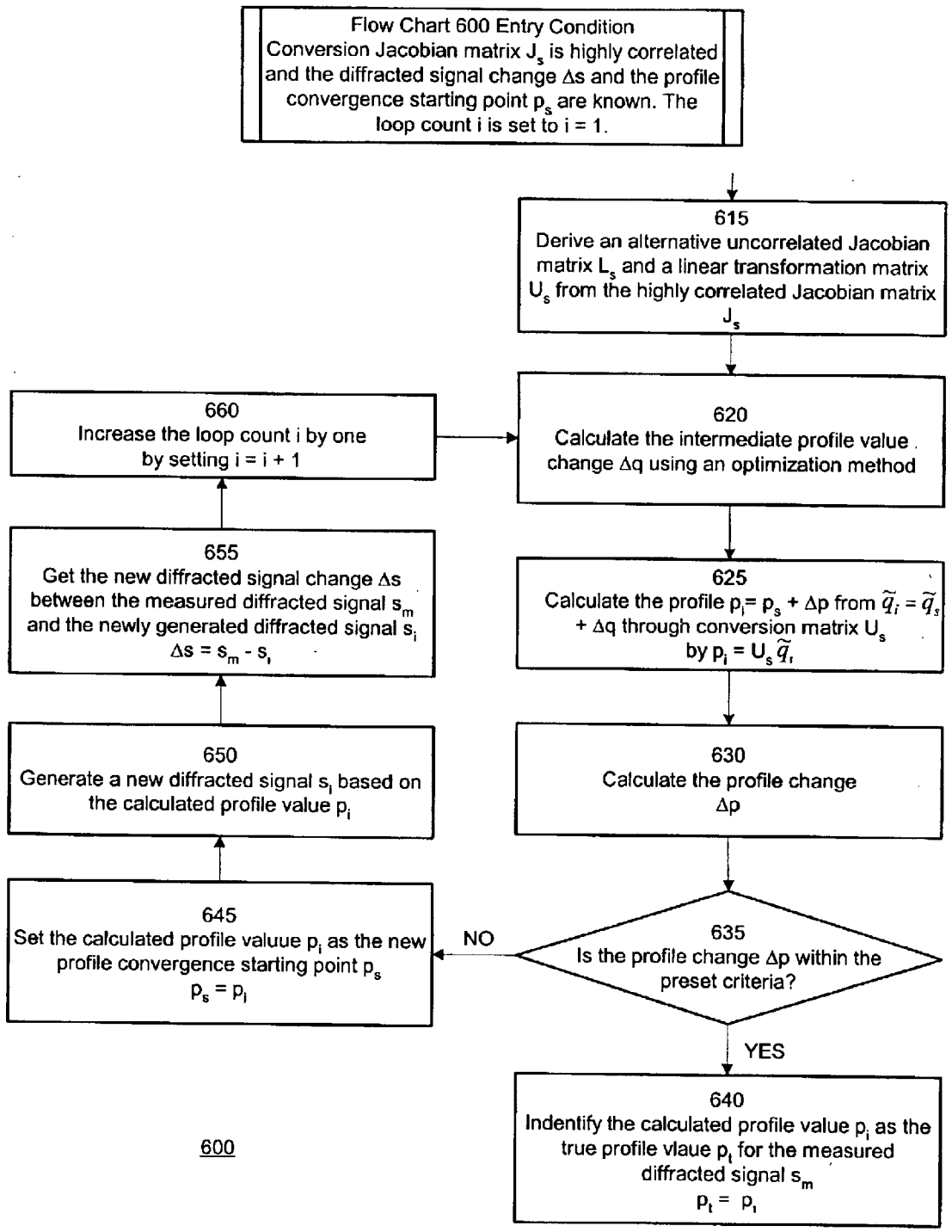
FIG. 6 is a detailed flow chart outlining steps for determining the true profile parameter value by using a second profile determining method in accordance with the embodiment depicted in FIG. 3.

Referring now to FIG. 6 in view of FIG. 3, a detailed flow chart 600 is shown outlining profile determining method B. Flow chart 600 is the detailed explanation for step 370 of flow chart 300 in FIG. 3. The entry condition for flow chart 600 is that the conversion Jacobian matrix $J_s$ is already evaluated (in step 350 of flow chart 300 in FIG. 3) to have highly correlated sensitivities of sample structure profile parameters. The diffraction signal change Δs between the measured diffraction signal $s_m$ and the nearest diffraction signal $s_s$ is computed (step 320 of flow chart 300). The profile parameter $p_s$ is obtained from profile library 140 (step 330 of flow chart 300). The profile parameter $p_s$, corresponding to the nearest diffraction signal $s_s$, is used as the starting point for converging to $p_t$. Moreover, the loop count i is set to one in order to keep track the number of iterations for the profile computation and diffraction signal simulation.

In step 615, the alternative uncorrelated Jacobian matrix $L_s$ and the linear transformation matrix $T_s$ are derived from the highly correlated Jacobian matrix $J_s$.

Specifically, for a given matrix $J_{s\ m\times n}$, the covariance matrix M can be written as:

$$M = \text{cov}(J_s) = (K^t K)/(m-1)$$

where:

$$K = J_s - \frac{1}{m}\begin{pmatrix} 1 & \cdots & 1 \\ \vdots & & \vdots \\ 1 & \cdots & 1 \end{pmatrix}_{m\times m} \times J_s.$$

Because sensitivities of sample structure profile parameters as provided by Jacobian matrix $J_s$ are highly correlated, another Jacobian matrix $L_s$ is derived through the matrix M. Matrix M can be diagonalized to obtain matrix N that is the cov($L_s$). In so doing, $L_s$ has sensitivities of sample structure profile parameters that are not correlated.

Specifically, since the matrix M is real and symmetrical, a linear transformation matrix $T_s$ exists and satisfies:

$$N = T_s^t M T_s$$

where N results from diagonalizing the matrix M, and N is the covariance matrix of the alternative uncorrelated Jacobian matrix $L_s$, and where:

$$L_s = J_s T_s.$$

That is:

$$\Delta s \approx J_s \Delta p \approx [\partial s/\partial p][\partial p/\partial q]\Delta \tilde{q} \approx J_s T_s \Delta \tilde{q} \approx L_s \Delta \tilde{q}$$

where:

$$J_s = [\partial s/\partial p],\ T_s = [\partial p/\partial q],\ L_s = [\partial s/\partial q].$$

In step 620, the intermediate profile parameter value change $\Delta \tilde{q}$ is determined using an optimization algorithm based on Δs.

In step 625, the profile parameter value change $p_1 = p_s + \Delta p$ is mapped by the linear transformation matrix $U_s$ from the intermediate profile parameter value change $$\tilde{q}_i = \tilde{q}_s + \Delta \tilde{q}$$

where $\tilde{q}$ is the mapping of P using the transformation matrix U from space P to $\tilde{Q}$:

$$p_i \approx U_s \tilde{q}_i,\ \text{wherein}\ U_s = \lambda I + (1-\lambda) T_s,$$

where $\lambda \in [0,1]$, and I is an identity matrix.

In step 630, the profile parameter value Δp is calculated, where i is the number of iterations for profile computation and diffraction signal simulation.

In step 635, the profile parameter value change Δp calculated in step 625 is evaluated to determine whether this profile parameter value change Δp satisfies the preset criteria. The preset criteria may be that certain error metric value is less than a preset value, or goodness of fit (GOF) is higher than a preset value, or the difference between the profile parameter values of the last two consecutive iterations is less than a present value. One exemplary matching test that is well known in the art is that of minimum mean square error. It is understood that other error metric algorithms may also be used.

In step 640, the profile parameter value change $\Delta p_1$ meets the preset criteria, and therefore, the profile parameter value $p_i$ calculated in step 630 is deemed as an acceptable approximation to the true profile parameter value $p_t$ for the measured diffraction signal $s_m$.

In step 645, since the profile parameter value change Δp does not meet the preset criteria, the profile parameter value $p_1$ calculated in step 625 is set as the new profile convergence starting point $p_s$:

$$p_s = p_1$$

where i is the number of iterations for the diffraction signal simulation and profile computation.

In step 650, a new diffraction signal $s_1$ is simulated by using RCWA method based on the profile parameter value $p_1$ calculated in step 630.

In step 655, the new diffraction signal change Δs between the measured diffraction signal $s_m$ and the newly simulated diffraction signal $s_1$ is computed as $$\Delta s = s_m - s_i.$$

In step 660, the loop count i is increased by one to keep track the number of iterations for diffraction signal simulation and profile computation. The profile parameter value computation loops back to step 620 and the calculation of the simulated diffraction signal and the profile parameter value is iterated until the profile parameter value change Δp calculated in step 625 meets the preset criteria.

The extraction of the profile parameter value considered an acceptable approximation of the true profile parameter value can be viewed as an optimization process. Exemplary optimization techniques include global optimization techniques such as genetic algorithm and local optimization techniques such as the steepest descent algorithm.

Figure 7:
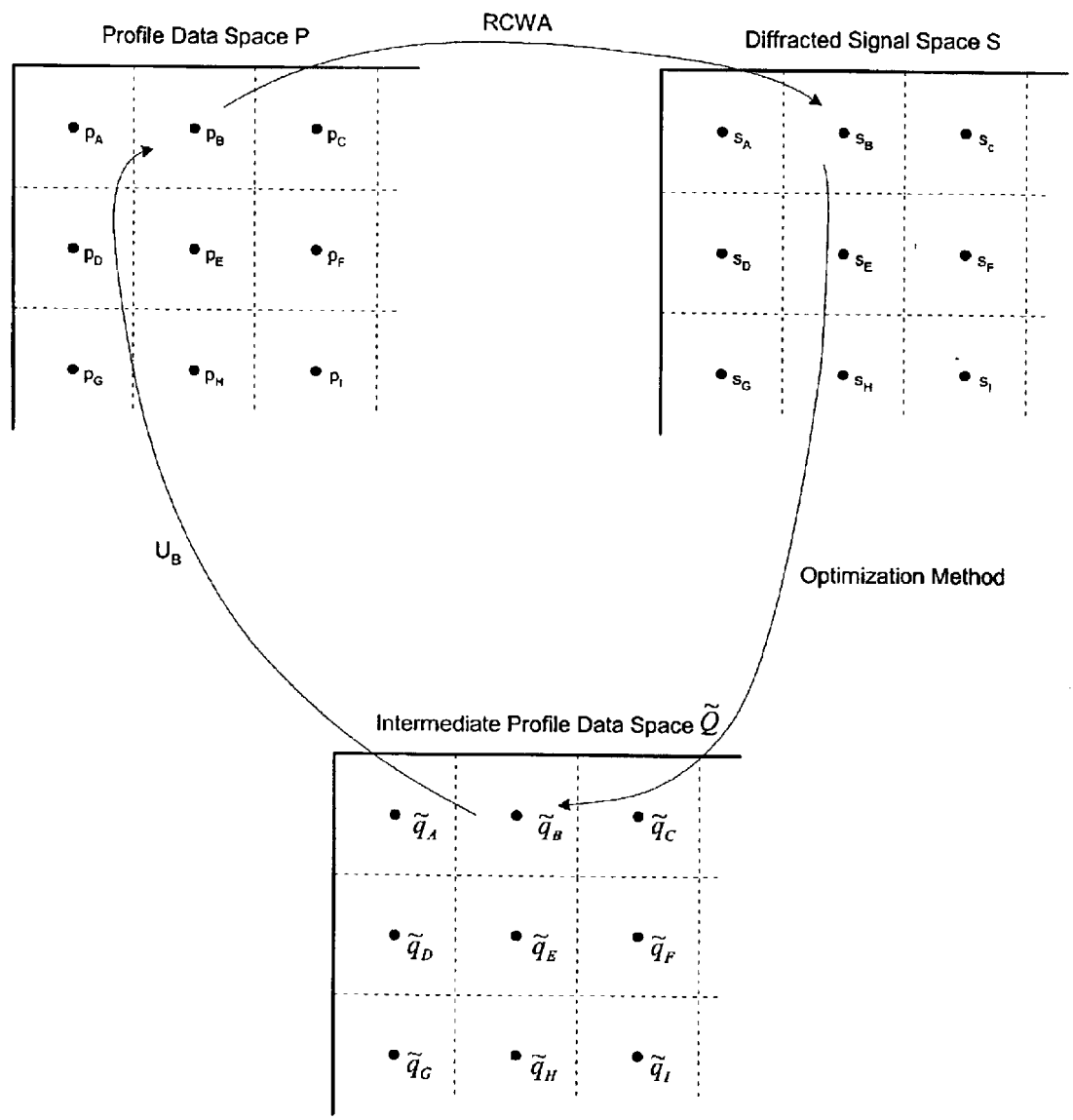
FIG. 7 is an illustration demonstrating the one-to-one relationship among the profile parameters, the diffraction signals, and the intermediate profile parameter values in their respective data spaces when the second profile determining method is used in accordance with one embodiment.

Referring now to FIG. 7 in view of FIG. 6, a graphical illustration 700 is shown demonstrating the one-to-one corresponding relationship among the profile parameters in a profile data space P, the diffraction signals in a diffraction signal data space S, and the intermediate profile parameter values in an intermediate profile data space $\tilde{Q}$ when profile determining method B is used.

In diagram 700, the dashed lines represent the neighborhood borders of the data points. The optimization algorithm is used to convert from the diffraction signal change $\Delta s$ within the neighborhood of $s_B$ in the diffraction signal data space S to the corresponding intermediate profile parameter value change $\Delta \tilde{q}$ within the neighborhood of $\tilde{q}_B$ in the intermediate profile data space $\tilde{Q}$.

The linear transformation matrix $U_B$ maps $\tilde{Q}$ to P. Specifically, $U_B$ is used to map $\tilde{q}_B$ (in the intermediate profile data space $\tilde{Q}$) to $p_B$ in the profile data space P.

RCWA method is used to simulate the diffraction signals in the diffraction signal data space S from the profile parameters in the profile data space P. The diffraction signal $s_B$ is simulated based on the profile parameter $p_B$.

Figure 8:
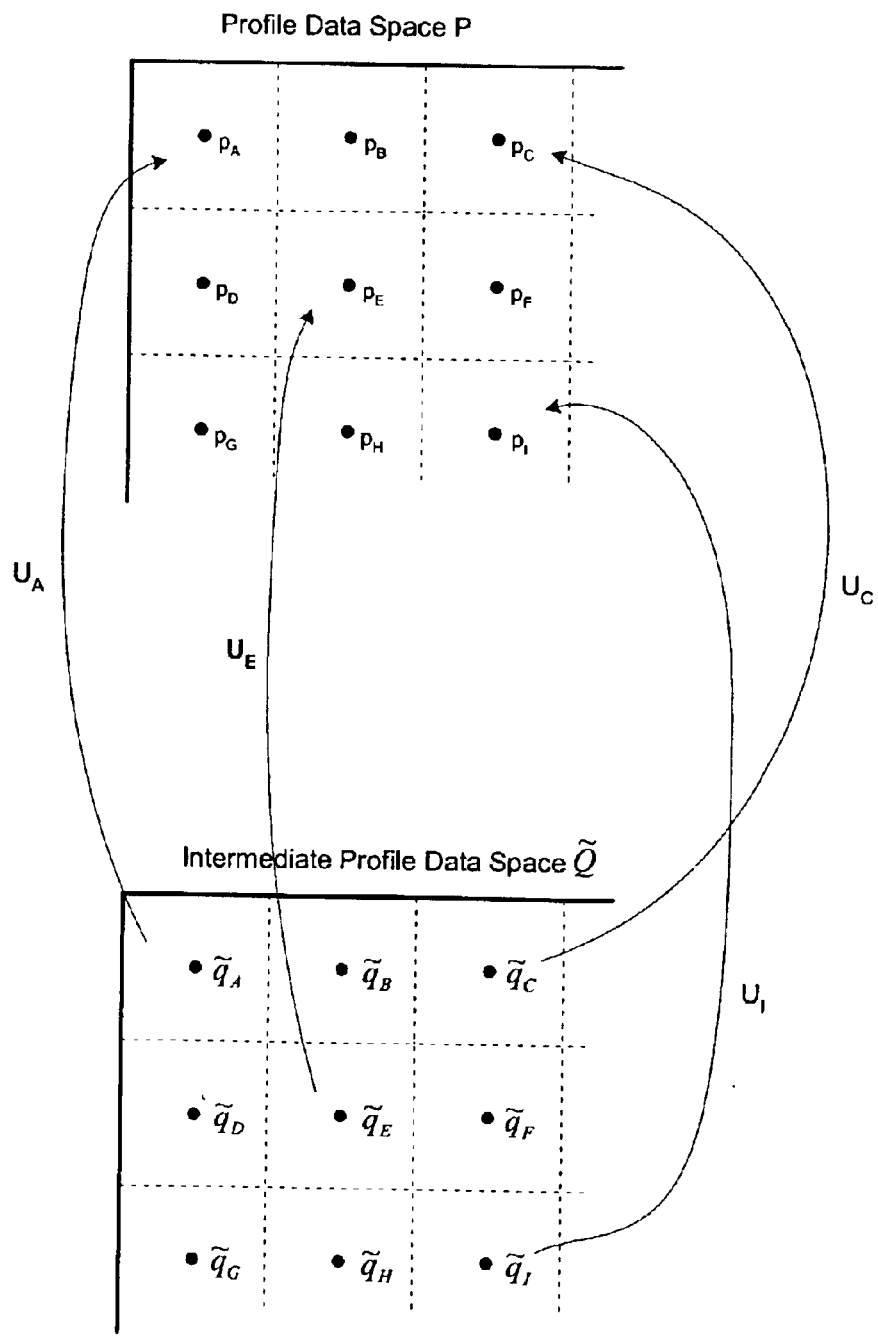
FIG. 8 is an illustration demonstrating the concept that the linear transformation matrix for a middle profile parameter point of a profile library can be used to perform the profile parameter value mapping from the intermediate profile data space to the profile data space for the whole profile library in accordance with one embodiment.

Referring now to FIG. 8, a graphical illustration 800 is shown demonstrating that a linear transformation matrix U for a profile point in a profile library can be used to perform the profile parameter value mapping from a domain of an intermediate profile data space $\tilde{Q}$ to a domain of a profile data space P in accordance with one embodiment.

As shown in diagram 800, a linear transformation matrix U exists for every profile parameter point (and its neighborhood) in a profile data space $\tilde{Q}$. On the other hand, the profile mapping process can be further simplified.

Specifically, the matrix U (i.e., $U_E$) of a point in the middle of a domain in a profile library can be used to perform all the profile mapping from the shown domain of the intermediate profile data space $\tilde{Q}$ to the shown domain of the profile data space P. In so doing, a Jacobian matrix (from $\tilde{Q}$ to S) can have a covariance matrix that deviates from a diagonal matrix. However, as understood herein, in domain $\tilde{Q}$ the size of the domain sharing one transformation matrix U is chosen to limit the deviation of the covariance matrix (of a Jacobian matrix) from a diagonal matrix.

The foregoing descriptions of specific embodiments have been presented for purposes of illustration and description. They are not intended to be exhaustive or to limit the invention to the precise forms disclosed. Obviously, many modifications and variations are possible in light of the above teaching. The embodiments were chosen and described in order to explain the principles and the application of the invention, thereby enabling others skilled in the art to utilize the invention in its various embodiments and modifications according to the particular purpose contemplated. The scope of the invention is intended to be defined by the claims appended hereto and their equivalents.

We claim:

1. A method of determining a profile parameter value in integrated circuit metrology comprising:
   a) determining a diffraction signal difference based on a measured diffraction signal and a previously generated diffraction signal;
   b) determining a first profile parameter value based on the previously generated diffraction signal;
   c) determining a first profile parameter value change based on the diffraction signal difference;
   d) determining a second profile parameter value based on the first profile parameter value change;
   e) determining a second profile parameter value change between the first and second profile parameter values;
   f) determining if the second profile parameter value change meets one or more preset criteria; and
   g) when the second profile parameter value change fails to meet the one or more preset criteria, iterating steps c) to g) using:
      as the diffraction signal difference in the iteration of step c), a diffraction signal difference determined based on the measured diffraction signal and a diffraction signal for the second profile parameter value previously determined in step d), and
      as the first profile parameter value in the iteration of step e), the second profile parameter value previously determined in step d).

2. The method of claim 1, wherein the measured diffraction signal was measured using an integrated circuit metrology system.

3. The method of claim 2, wherein the measured diffraction signal is a signal obtained by measuring light diffracted from a sample using an optical metrology system.

4. The method of claim 1, wherein the previously generated diffraction signal is a best match diffraction signal obtained from a library of diffraction signals.

5. The method of claim 1, wherein the previously generated diffraction signal is determined using a global optimization algorithm.

6. The method of claim 1, wherein the previously generated diffraction signal is determined using a combination of a global and local optimization algorithm.

7. The method of claim 1 further comprising:
   obtaining a first Jacobian matrix based on the previously generated diffraction signal.

8. The method of claim 7 further comprising:
   determining if the first Jacobian matrix has a degree of correlation above a threshold level;
   when the degree of correlation of the first Jacobian matrix is above the threshold level, determining profile parameter values using a first method; and
   when the degree of correlation of the first Jacobian matrix is at or below the threshold level, determining profile parameter values using a second method.

9. The method of claim 8, wherein the first method comprises performing steps a) to g) of claim 1, and wherein the second method comprises performing only steps a) and b) of claim 1 then performing the following steps:
   a) determining a profile parameter value change based on the inverse of the first Jacobian matrix and the diffraction signal difference determined in step a) of claim 1,
   b) determining a second profile parameter value based on the first profile parameter value determined in step b) of claim 1 and the profile parameter value change,
   c) determining if the profile parameter value change meets one or more preset criteria, and
   d) when the profile parameter value change fails to meet the one or more preset criteria, iterating steps a) to d) using:
      as the first Jacobian matrix in the iteration of step a), a Jacobian matrix obtained based on a diffraction signal for the second profile parameter value previously determined in step b),
      as the diffraction signal difference in the iteration of step a), a diffraction signal difference determined based on the measured diffraction signal and the diffraction signal for the second profile parameter value previously determined in step b), and as the first parameter value in the iteration of step b), the second profile parameter value previously determined in step b).

10. The method of claim 7 further comprising:
obtaining a second Jacobian matrix based on the first Jacobian matrix,
wherein the second Jacobian matrix has a degree of correlation less than the first Jacobian matrix; and
obtaining a linear transformation matrix based on the first Jacobian matrix.

11. The method of claim 10, wherein the first profile parameter value change is determined using the second Jacobian matrix.

12. The method of claim 10, wherein the second profile parameter value is determined using the linear transformation matrix.

13. The method of claim 10, wherein obtaining a linear transformation matrix comprises:
determining a first covariance matrix of the first Jacobian matrix;
determining a second covariance matrix of the second Jacobian matrix; and
determining the linear transformation matrix based on the first and second covariance matrices.

14. The method of claim 1, wherein the one or more preset criteria include a goodness of fit (GOF) metric.

15. The method of claim 1, wherein the one or more preset criteria include a minimum mean square error metric.

16. The method of claim 1 further comprising:
incrementing a loop count when an iteration is performed; and
terminating the iterations when a predetermined maximum value of the loop count is reached.

17. The method of claim 1, wherein the previously generated diffraction signal was generated using a Rigorous Coupled Wave Analysis.

18. A method of determining a profile parameter value in integrated circuit metrology comprising:
determining a diffraction signal difference based on a measured diffraction signal and a previously generated diffraction signal;
determining a first profile parameter value based on the previously generated diffraction signal;
obtaining a first Jacobian matrix based on the previously generated diffraction signal;
determining if the first Jacobian matrix has a degree of correlation above a threshold level;
when the degree of correlation of the first Jacobian matrix is above the threshold level, using a first profile parameter value determination method; and
when the degree of correlation of the first Jacobian matrix is at or below the threshold level, using a second profile parameter value determination method.

19. The method of claim 18, wherein the first profile parameter value determination method comprises:
a) determining a first profile parameter value change based on the diffraction signal difference;
b) determining a second profile parameter value based on the first profile parameter value change;
c) determining a second profile parameter value change between the first and second profile parameter values;
d) determining if the second profile parameter value change meets one or more preset criteria; and
e) when the second profile parameter value change fails to meet the one or more preset criteria, iterating steps a) to e) using:

as the diffraction signal difference in the iteration of step a), a diffraction signal difference determined based on the measured diffraction signal and a diffraction signal for the second profile parameter value previously determined in step b), and
as the first profile parameter value in the iteration of step c), the second profile parameter value previously determined in step b).

20. The method of claim 18, wherein the second profile parameter value determination method comprises:
a) determining a profile parameter value change based on the inverse of the first Jacobian matrix and the diffraction signal difference;
b) determining a second profile parameter value based on the first profile parameter value and the profile parameter value change;
c) determining if the profile parameter value change meets one or more preset criteria; and
d) when the profile parameter value change fails to meet the one or more preset criteria, iterating steps a) to d) using:
as the first Jacobian matrix in the iteration of step a), a Jacobian matrix obtained based on a diffraction signal for the second profile parameter value previously determined in step b),
as the diffraction signal difference in the iteration of step a), a diffraction signal difference determined based on the measured diffraction signal and the diffraction signal for the second profile parameter value previously determined in step b), and
as the first parameter value in the iteration of step b), the second profile parameter value previously determined in step b).

21. The method of claim 18 further comprising:
obtaining a second Jacobian matrix based on the first Jacobian matrix,
wherein the second Jacobian matrix has a degree of correlation less than the first Jacobian matrix; and
obtaining a linear transformation matrix based on the first Jacobian matrix.

22. The method of claim 21, wherein obtaining a linear transformation matrix comprises:
determining a first covariance matrix of the first Jacobian matrix;
determining a second covariance matrix of the second Jacobian matrix; and
determining the linear transformation matrix based on the first and second covariance matrices.

23. A metrology system to determine a profile parameter value, the system comprising:
a signal source configured to direct a signal at a sample;
a signal detector configured to measure a diffraction signal diffracted from the sample; and
a profile application server configured to:
a) determine a diffraction signal difference based on the measured diffraction signal and a previously generated diffraction signal;
b) determine a first profile parameter value based on the previously generated diffraction signal;
c) determine a first profile parameter value change based on the diffraction signal difference;
d) determine a second profile parameter value based on the first profile parameter value change;
e) determine a second profile parameter value change between the first and second profile parameter values;

f) determine if the second profile parameter value change meets one or more preset criteria; and g) when the second profile parameter value change fails to meet the one or more preset criteria, iterate steps c) to g) using:

as the diffraction signal difference in the iteration of step c), a diffraction signal difference determined based on the measured diffraction signal and a diffraction signal for the second profile parameter value previously determined in step d), and as the first profile parameter value in the iteration of step e), the second profile parameter value previously determined in step d).

24. The system of claim 23 further comprising:
an optical metrology system, wherein the signal source and signal detector are elements of the optical metrology system, and wherein the signal directed at the sample is light.

25. The system of claim 23 further comprising:
a library of diffraction signals, wherein the previously generated diffraction signal is a best match diffraction signal from the library of diffraction signals.

26. The system of claim 23 further comprising:
a library of Jacobian matrices.

27. The system of claim 23 further comprising:
an IC fabrication unit, wherein the profile application server provides the second profile parameter value to the IC fabrication unit when the second profile parameter value change meets the one or more preset criteria.

28. A metrology system to determine a profile parameter value, the system comprising:
a library of previously generated diffraction signals; and
a profile application server configured to:
a) determine a diffraction signal difference based on a measured diffraction signal and a previously generated diffraction signal from the library;
b) determine a first profile parameter value based on the previously generated diffraction signal;
c) determine a first profile parameter value change based on the diffraction signal difference;
d) determine a second profile parameter value based on the first profile parameter value change;
e) determine a second profile parameter value change between the first and second profile parameter values;
f) determine if the second profile parameter value change meets one or more preset criteria; and
g) when the second profile parameter value change fails to meet the one or more preset criteria, iterate steps c) to g) using:

as the diffraction signal difference in the iteration of step c), a diffraction signal difference determined based on the measured diffraction signal and a diffraction signal for the second profile parameter value previously determined in step d), and as the first profile parameter value in the iteration of step e), the second profile parameter value previously determined in step d).

29. The system of claim 28 further comprising:
an IC fabrication unit, wherein the profile application server provides the second profile parameter value to the IC fabrication unit when the second profile parameter value change meets the one or more preset criteria.

30. A computer-readable storage medium containing computer executable code to determine a profile parameter value in integrated circuit metrology by instructing a computer to operate as follows:

a) determine a diffraction signal difference based on a measured diffraction signal and a previously generated diffraction signal;

b) determine a first profile parameter value based on the previously generated diffraction signal;

c) determine a first profile parameter value change based on the diffraction signal difference;

d) determine a second profile parameter value based on the first profile parameter value change;

e) determine a second profile parameter value change between the first and second profile parameter values;

f) determine if the second profile parameter value change meets one or more preset criteria; and g) when the second profile parameter value change fails to meet the one or more preset criteria, iterate c) to g) using:

as the diffraction signal difference in the iteration of c), a diffraction signal difference determined based on the measured diffraction signal and a diffraction signal for the second profile parameter value previously determined in d), and as the first profile parameter value in the iteration of e), the second profile parameter value previously determined in d).

31. The computer-readable storage medium of claim 30, wherein the measured diffraction signal is a signal obtained by measuring light diffracted from a sample using an optical metrology system.

32. The computer-readable storage medium of claim 30, wherein the previously generated diffraction signal is a best match diffraction signal obtained from a library of diffraction signals.

33. The computer-readable storage medium of claim 30, wherein the previously generated diffraction signal is determined using a global optimization algorithm.

34. The computer-readable storage medium of claim 30, wherein the previously generated diffraction signal is determined using a combination of a global and local optimization algorithm.

35. The computer-readable storage medium of claim 30, wherein the computer is further instructed to operate as follows:
obtain a first Jacobian matrix based on the previously generated diffraction signal.

36. The computer-readable storage medium of claim 35, wherein the computer is further instructed to operate as follows:
determine if the first Jacobian matrix has a degree of correlation above a threshold level;
when the degree of correlation of the first Jacobian matrix is above the threshold level, determine profile parameter values using a first method; and
when the degree of correlation of the first Jacobian matrix is at or below the threshold level, determine profile parameter values using a second method.

37. The computer-readable storage medium of claim 36, wherein the first method comprises performing a) to g) of claim 30, and wherein the second method comprises performing only a) and b) of claim 30 then performing the following steps:
a) determining a profile parameter value change based on the inverse of the first Jacobian matrix and the diffraction signal difference determined in step a) of claim 30,
b) determining a second profile parameter value based on the first profile parameter value determined in step b) of claim 30 and the profile parameter value change, c) determining if the profile parameter value change meets one or more preset criteria, and d) when the profile parameter value change fails to meet the one or more preset criteria, iterating steps a) to d) using:

as the first Jacobian matrix in the iteration of step a), a Jacobian matrix obtained based on a diffraction signal for the second profile parameter value previously determined in step b), as the diffraction signal difference in the iteration of step a), a diffraction signal difference determined based on the measured diffraction signal and the diffraction signal for the second profile parameter value previously determined in step b), and as the first parameter value in the iteration of step b), the second profile parameter value previously determined in step b).

38. The computer-readable storage medium of claim 35, wherein the computer is further instructed to operate as follows:

obtain a second Jacobian matrix based on the first Jacobian matrix, wherein the second Jacobian matrix has a degree of correlation less than the first Jacobian matrix; and obtain a linear transformation matrix based on the first Jacobian matrix.

39. The computer-readable storage medium of claim 38, wherein the first profile parameter value change is determined using the second Jacobian matrix.

40. The computer-readable storage medium of claim 38, wherein the second profile parameter value is determined using the linear transformation matrix.

41. The computer-readable storage medium of claim 38, wherein obtain a linear transformation matrix comprises:

determine a first covariance matrix of the first Jacobian matrix;

determine a second covariance matrix of the second Jacobian matrix; and determine the linear transformation matrix based on the first and second covariance matrices.

42. The computer-readable storage medium of claim 30, wherein the one or more preset criteria include a goodness of fit (GOF) metric.

43. The computer-readable storage medium of claim 30, wherein the one or more preset criteria include a minimum mean square error metric.

44. The computer-readable storage medium of claim 30, wherein the computer is further instructed to operate as follows:

increment a loop count when an iteration is performed; and terminate the iterations when a predetermined maximum value of the loop count is reached.

45. The computer-readable storage medium of claim 30, wherein the previously generated diffraction signal was generated using a Rigorous Coupled Wave Analysis.

* * * * *